US012589119B2

(12) United States Patent
O'Heeron et al.

(10) Patent No.: US 12,589,119 B2
(45) Date of Patent: Mar. 31, 2026

(54) TREATMENT OF CACHEXIA USING FIBROBLAST CELLS AND PRODUCTS THEREOF

(71) Applicant: FIBROBIOLOGICS, INC., Houston, TX (US)

(72) Inventors: Pete O'Heeron, Houston, TX (US); Thomas Ichim, San Diego, CA (US)

(73) Assignee: FIBROBIOLOGICS, INC., Houston, TX (US)

( * ) Notice: Subject to any disclaimer, the term of this patent is extended or adjusted under 35 U.S.C. 154(b) by 857 days.

(21) Appl. No.: 17/309,177

(22) PCT Filed: Nov. 4, 2019

(86) PCT No.: PCT/US2019/059678
§ 371 (c)(1),
(2) Date: May 3, 2021

(87) PCT Pub. No.: WO2020/093050
PCT Pub. Date: May 7, 2020

(65) Prior Publication Data
US 2022/0023349 A1     Jan. 27, 2022

Related U.S. Application Data

(60) Provisional application No. 62/755,542, filed on Nov. 4, 2018.

(51) Int. Cl.
| | |
|---|---|
| *A61K 35/33* | (2015.01) |
| *A61P 1/14* | (2006.01) |
| *A61P 21/00* | (2006.01) |
| *C12N 5/077* | (2010.01) |

(52) U.S. Cl.
CPC ............... *A61K 35/33* (2013.01); *A61P 1/14* (2018.01); *A61P 21/00* (2018.01); *C12N 5/0656* (2013.01)

(58) Field of Classification Search
CPC ............. A61K 35/33; A61P 21/00; A61P 1/14
See application file for complete search history.

(56) References Cited

U.S. PATENT DOCUMENTS

| | | | | |
|---|---|---|---|---|
| 5,188,817 | A | 2/1993 | Ozick | |
| 7,569,385 | B2 * | 8/2009 | Haas | C12N 5/0605 435/402 |
| 7,850,983 | B2 | 12/2010 | Sevrain et al. | |
| 9,173,906 | B2 | 11/2015 | Rolland et al. | |
| 9,603,878 | B2 | 3/2017 | Berry et al. | |
| 10,987,325 | B2 | 4/2021 | Bradley et al. | |
| 11,034,934 | B2 * | 6/2021 | O'Heeron | A61P 9/00 |
| 11,819,555 | B2 | 11/2023 | O'Heeron | |
| 2002/0037279 | A1 * | 3/2002 | Vandenburgh | A61K 38/1875 435/325 |
| 2004/0107453 | A1 | 6/2004 | Furcht et al. | |

| | | | | |
|---|---|---|---|---|
| 2005/0147596 | A1 | 7/2005 | Keller et al. | |
| 2005/0170510 | A1 | 8/2005 | Huang et al. | |
| 2006/0233766 | A1 | 10/2006 | Messina et al. | |
| 2009/0202500 | A1 | 8/2009 | Tamai et al. | |
| 2014/0314726 | A1 | 10/2014 | O'Heeron et al. | |
| 2016/0375098 | A1 | 12/2016 | Kadouri et al. | |
| 2017/0224740 | A1 | 8/2017 | Sing et al. | |
| 2017/0281685 | A1 | 10/2017 | Bogin et al. | |
| 2018/0071342 | A1 | 3/2018 | Ichim et al. | |
| 2018/0133258 | A1 * | 5/2018 | Ichim | A61K 35/28 |
| 2018/0195044 | A1 | 7/2018 | O'Heeron et al. | |
| 2019/0101547 | A1 | 4/2019 | Berger et al. | |
| 2019/0136299 | A1 | 5/2019 | Putignani et al. | |

FOREIGN PATENT DOCUMENTS

| | | |
|---|---|---|
| JP | H06502406 A | 3/1994 |
| JP | 2018511599 A | 4/2018 |
| WO | WO-1992006702 A1 | 4/1992 |
| WO | 2005/017117 A2 | 2/2005 |
| WO | WO-2007035843 A2 | 3/2007 |
| WO | WO-2007149548 A2 | 12/2007 |
| WO | WO-2010071862 A1 | 6/2010 |
| WO | WO-2011015862 A1 | 2/2011 |
| WO | WO-2012004566 A1 | 1/2012 |
| WO | WO-2013070880 A1 | 5/2013 |
| WO | WO-2014026012 A2 | 2/2014 |
| WO | WO-2015035395 A1 | 3/2015 |
| WO | WO-2016161290 A1 | 10/2016 |
| WO | WO-2017023689 A1 | 2/2017 |
| WO | WO-2018013612 A1 | 1/2018 |

(Continued)

OTHER PUBLICATIONS

Hematti P. Mesenchymal stromal cells and fibroblasts: a case of mistaken identity? Cytotherapy. May 2012;14(5):516-21. doi: 10.3109/14653249.2012.677822. Epub Mar. 29, 2012. PMID: 22458957. (Year: 2012).*

Hematti (Cytotherapy. May 2012;14(5):516-21. doi: 10.3109/14653249.2012.677822. Epub Mar. 29, 2012 (Year: 2012).*

Denu et al (Acta Haematol. 2016; 136(2): 85-97. doi: 10.1159/000445096.) (Year: 2016).*

Ichim et al. (J Transl Med (2018) 16:212 https://doi.org/10.1186/s12967-018-1536-1) (Year: 2018).*

Amitani et al., "Mechanism and Nutrition in Cachexia," Jpn. J. Psychosom. Med., 56(10):1013-1022, 2016. (English abstract on p. 1022.).

(Continued)

*Primary Examiner* — Fereydoun G Sajjadi
*Assistant Examiner* — Joel D Levin
(74) *Attorney, Agent, or Firm* — Norton Rose Fulbright LLP

(57) ABSTRACT

Disclosed are methods and compositions related to treatment, amelioration or prevention of cachexia or inflammation related to cachexia in a subject. As disclosed, cachexia or inflammation related to cachexia can be treated, ameliorated or prevented by the administration of an effective amount of a composition including immune-modulating fibroblasts to the subject.

12 Claims, 1 Drawing Sheet

(56)                References Cited

FOREIGN PATENT DOCUMENTS

| WO | WO-2018015945 A2 | 1/2018 |
| WO | WO/2018/083700 | 5/2018 |
| WO | WO/2018/132594 | 7/2018 |
| WO | WO-2018195308 A1 | 10/2018 |
| WO | WO-2019094617 A1 | 5/2019 |
| WO | WO-2019108756 A1 | 6/2019 |
| WO | WO-2019191830 A1 | 10/2019 |
| WO | WO-2019213518 A1 | 11/2019 |
| WO | WO-2020093050 A2 | 5/2020 |
| WO | WO-2020093051 A1 | 5/2020 |
| WO | WO-2020144380 A1 | 7/2020 |
| WO | WO-2020146874 A1 | 7/2020 |
| WO | WO-2021050583 A1 | 3/2021 |
| WO | WO-2021097423 A1 | 5/2021 |
| WO | WO-2021134081 A1 | 7/2021 |
| WO | WO-2021178395 A1 | 9/2021 |
| WO | WO-2021211386 A1 | 10/2021 |
| WO | WO-2021216460 A1 | 10/2021 |
| WO | WO-2021232064 A2 | 11/2021 |
| WO | WO-2022047486 A2 | 3/2022 |

OTHER PUBLICATIONS

English Translation of Office Communication issued in Japanese Patent Application No. 2021-524163, dated Jul. 26, 2023.

Carson et al., "Interleukin-6 as a Key Regulator of Muscle Mass during Chachexia", Exercise and Sport Sciences Reviews, Oct. 2010, vol. 38, No. 4, pp. 168-176.

Meazza et al., "Effect of Growth Hormone (GB) on the Immune System", Pediatric Endocrinology Reviews, Aug. 2004, vol. 1, Suppl. 3, pp. 490-495.

Denu et al., "Fibroblasts and Mesenchymal Stromal/Stem Cells are Phenotypically Indistinguishable," Acta Haematologica, 136(2):85-97, 2016.

Extended European Search Report issued in European Patent Application No. 19878537.0, dated Jun. 22, 2022.

Ichim et al., "Fibroblasts as a practical alternative to mesenchymal stem cells," Journal of Translational Medicine, 16(1), pp. 1-9, 2018.

Jordana et al., "Immune-inflammatory functions of fibroblasts," European Respiratory Journal, 7(12):2212-2222, 1994.

American College of Surgeons "Best Practices Guidelines: The Management of Traumatic Brain Injury," 2024, 99 pages.

Anderson J.D., et al., "Mesenchymal Stem Cell-Based Therapy for Ischemic Stroke," Chinese Neurosurgical Journal, Nov. 1, 2016, vol. 02, No. 01, 6 pages. doi: 10.1186/s41016-016-0053-4, Retrieved from the Internet: URL: http://link.springer.com/content/pdf/10.1186/s41016-016-0053-4.pdf.

Arbelaez-Quintero I., et al., "To Use or Not to Use Metformin in Cerebral Ischemia: A Review of the Application of Metformin in Stroke Rodents," Stroke Research and Treatment, 2017, vol. 2017, 13 pages.

Balducci L., et al., "Chapter 30: The Differences Between Mesenchymal Stroma Cells and Fibroblasts," in: Atkinson K., The Biology and Therapeutic Application of Mesenchymal Cells, John Wiley & Sons, Inc., 2017, pp. 441-455.

Balducci L., et al., "The Differences Between Mesenchymal Stromal Cells and Fibroblasts," The Biology and Therapeutic Application of Mesenchymal Cells, K. Atkinson (ed.), John Wiley & Sons, Inc., 2017, pp. 441-455.

Bhang Sh, et al., "Basic fibroblast growth factor promotes bone marrow stromal cell transplantation-mediated neural regeneration in traumatic brain injury," Biochemical and Biophysical Research Communications, 2007, vol. 359, No. 1, pp. 40-45.

Caplan H., et al., "Mesenchymal Stromal Cell Therapeutic Delivery: Translational Challenges to Clinical Application," Frontiers in Immunology, 2019, vol. 10, art. 1645, 15 pages.

Chen S.J., et al., "Brain-Derived Neurotrophic Factor-Transfected and Nontransfected 3T3 Fibroblasts Enhance Migratory Neuroblasts and Functional Restoration in Mice With Intracerebral Hemorrhage," Journal of Neuropathology & Experimental Neurology, Dec. 2012, vol. 71, No. 12, pp. 1123-1136.

Chou P.C., et al., "Intracerebral Transplantation of Erythropoietin-Producing Fibroblasts Facilitates Neurogenesis and Functional Recovery in an Ischemic Stroke Model," Brain and Behavior, Feb. 28, 2019, vol. 09, 11 pages.

Cohen S.P., et al., "A Double-Blind, Placebo-Controlled, Dose-Response Pilot Study Evaluating Intradiscal Etanercept in Patients with Chronic Discogenic Low Back Pain or Lumbosacral Radiculopathy," Anesthesiology, Jul. 2007, vol. 107, No. 01, pp. 99-105.

Cona L.A., "Stem Cell Therapy for TBI: Mechanisms and Effectiveness," DVCSTEM, Apr. 9, 2025, 17 pages.

Cosme et al. "Hypoxia-Induced Changes in the Fibroblast Secretome, Exosome, and Whole-Cell Proteome Using Cultured, Cardiac-Derived Cells Isolated from Neonatal Mice", Journal of Proteome Research. Aug. 4, 2017, Epub Jul. 6, 2017, vol. 16, No. 8; pp. 2836-2847.

Costa-Almeida R., et al., "Fibroblasts as Maestros Orchestrating Tissue Regeneration," Journal of Tissue Engineering and Regenerative Medicine, Jan. 1, 2018, vol. 12, No. 01, doi: 10.1002/term.2405, pp. 240-251, Retrieved from the Internet: URL: https://api.wiley.com/onlinelibrary/tdm/v1/articles/10.1002%2Fterm.2405, XP055956264.

Cox CS, "Cellular therapy for traumatic neurological injury," Pediatric Research, vol. 83, No. 1, pp. 325-332 (Jan. 2018).

Cox C.S., et al., "Treatment of Sever Adult Traumatic Brain Injury using Bone Marrow Mononuclear Cells," Stem Cells, Nov. 23, 2016, 28 pages.

Cox J.R., et al., "Treatment of Severe Adult Traumatic Brain Injury Using Bone Marrow Mononuclear Cells," Stem Cells, Nov. 1, 2016, vol. 35, pp. 1065-1079.

Dekosky S.T., et al., " Interleukm-1 Receptor Antagonist Suppresses Neurotrophin Response in Injured Rat Brain," Annals of Neurology, Jan. 1996, vol. 39, No. 01, 02 Pages.

Denu R.A., et al., "Fibroblasts and Mesenchymal Stromal/Stem Cells are Phenotypically Indistinguishable," Acta Haematologhy, May 18, 2016, vol. 136, No. 02, pp. 85-97.

English translation of Office Communication issued in Japanese Patent Application No. 2021-524164, dated Jul. 14, 2023. 16 pages.

English translation of Office Communication issued in Japanese Patent Application No. 2021-525028, dated Sep. 5, 2023, 10 pages.

Extended European Search Report issued in European Application No. 22896789.9, mailed on Sep. 25, 2025, 07 pages.

Extended European Search Report issued in European Patent Application No. 19881814.8, dated Sep. 21, 2022, 09 pages.

Extended European Search Report issued in European Patent Application No. 20862683.8, dated Sep. 27, 2023, 09 pages.

Extended European Search Report issued in European Patent Application No. 20886462.9, dated Oct. 13, 2023. 9 pages.

Extended European Search Report issued in European Patent Application No. 24182563.7, dated Nov. 8, 2024, 8 pages.

Extended European Search Report issued in European Patent Application No. 19878521.4, dated Oct. 7, 2022, 10 pages.

Fries K.M., et al., "Evidence of Fibroblast Heterogeneity and the Role of Fibroblast Subpopulations in Fibrosis," Clinical Immunology and Immunopathology, vol. 72, No. 3, 1994, pp. 283-292.

Hematti P., "Mesenchymal Stromal Cells and Fibroblasts: A Case of Mistaken Identity," Cytotherapy, Mar. 29, 2012, vol. 14, pp. 516-521.

Huang H.I., et al., "Multilineage Differentiation Potential of Fibroblast-like Stromal Cells Derived from Human Skin," Tissue Engineering Part A, US, May 1, 2010, vol. 16, No. 05, doi:10.1089/ten.tea.2009.0431, pp. 1491-1501.

Huangfu, D. et al. "Induction of Pluripotent Stem Cells from Primary Human Fibroblasts with Only Oct4 and Sox2," Nature Biotechnology, vol. 26, No. 11. Nov. 2008, pp. 12691275.

International Search Report and Written Opinion for Application No. PCT/US2021/070642, dated Aug. 16, 2021, 10 pages.

International Search Report and Written Opinion for Application No. PCT/US2021/071296, dated Feb. 15, 2022, 15 pages.

(56) References Cited

OTHER PUBLICATIONS

International Search Report and Written Opinion for International Application No. PCT/US2019/030596, mailed Jul. 12, 2019, 9 Pages.

International Search Report and Written Opinion for International Application No. PCT/US2019/059678, mailed Jan. 27, 2020, 10 Pages.

International Search Report and Written Opinion for International Application No. PCT/US2019/060397, mailed Feb. 18, 2020, 8 Pages.

International Search Report and Written Opinion for International Application No. PCT/US2020/060724, mailed Mar. 10, 2021, 9 Pages.

International Search Report and Written Opinion Issued in International Application No. PCT/US2019/059683, Mailed on Jan. 30, 2020, 16 pages.

International Search Report and Written Opinion issued in International Application No. PCT/US2020/049949, mailed Jan. 7, 2021, 12 pages.

Invitation to Pay Additional Fees issued in International Application No. PCT/US2021/071296, dated Dec. 2, 2021, 2 pages.

Kahounova Z., et al., "The Fibroblast Surface Markers FAP, Anti-Fibroblast, and FSP are Expressed by Cells of Epithelial Origin and may be Altered during Epithelial to Mesenchymal Transition," Cytometry Part A, Apr. 6, 2017, pp. 941-951.

Kaur J., et al., "Mental Imagery as a Rehabilitative Therapy for Neuropathic Pain in People With Spinal Cord Injury: A Randomized Controlled Trial," Neurorehabilitation and Neural Repair, vol. 34, No. 11, 2020, pp. 1038-1049.

Lee S.B., et al., "Identification of a Distinct Subpopulation of Fibroblasts From Murine Dermis: CD73() CD105(+) as Potential Marker of Dermal Fibroblast Subset With Multipotency," Cell Biology International, vol. 40, No. 9, 2016, 01 Page.

Lefvre, S. et al., "Synovial Fibroblasts Spread Rheumatoid Arthritis to Unaffected Joints," Nature Medicine, vol. 15, No. 12, Dec. 2009, pp. 1414-1420.

Li S., et al., "Characteristics of Human Umbilical Cord Mesenchymal Stem Cells during Ex Vivo Expansion," Molecular Medicine Reports, Jun. 25, 2015, pp. 4320-4325.

Li S., et al., "Conversion of Astrocytes and Fibroblasts into Functional Noradrenergic Neuron," Cell Reports, Jul. 16, 2019, vol. 28, No. 03, 33 pages.

Lim J.Y., et al., "Therapeutic Effects of Human Umbilical Cord Blood-derived Mesenchymal Stem Cells After Intrathecal Administration by Lumbar Puncture in a Rat Model of Cerebral Ischemia," Stem Cell Research & Therapy, Sep. 22, 2011, vol. 02, No. 38, 13 pages.

Lin, W., et al., "Mesenchymal Stem Cells Homing to Improve Bone Healing," Journal of Orthopaedic Translation, vol. 9, 2017, pp. 1927.

Liu S., et al., "Mouse-induced Pluripotent Stem Cells Generated Under Hypoxic Conditions in the Absence of Viral Infection and Oncogenic Factors and Used for Ischemic Stroke Therapy," Stem Cells and Development, 2014, 23(4), pp. 421-433.

Liu X., et al., "The Immunogenicity and Immune Tolerance of Pluripotent Stem Cell Derivatives," Frontiers in Immunology, 2017, vol. 8, art. 645, 6 pages.

Loupy A., et al., "Immune Response After Pig-to-human Kidney Xenotransplantation: a Multimodal Phenotyping Study," Lancet, 2023, vol. 402, pp. 1158-1169.

Lv F.J., et al., "Concise Review: The Surface Markers and Identity of Human Mesenchymal Stem Cells," Stem Cells, May 23, 2014, vol. 32, pp. 1408-1419.

Maleki M., et al., "Comparison of Mesenchymal Stem Cell Markers in Multiple Human Adult Stem Cells," International Journal of Stem Cells, 2014, vol. 07, No. 02, pp. 118-126.

Maqbool A., et al., "The Substrate-binding protein in bacterial abc transporters: dissecting roles in the evolution of substrate specificity," Biochemical Society Transactions, 2015, vol. 43(5), pp. 10111017.

Mastri M., et al., "Enhancing the Efficacy of Mesenchymal Stem Cell Therapy," World Journal of Stem Cells, Apr. 26, 2014, vol. 06, No. 02, ISSN 0005144886, pp. 82-93.

Mcginnis A., et al., "Animal Models of Pain and Anti-inflammatory Treatments," in Neuroimmune Interactions in Pain, Springer Nature Switzerland AG, 2023, pp. 43-85.

Morita, "A Subpopulation of Fibroblasts Muse Cells, Ameliorate Rat Stroke Model," The Journal of Physiological Sciences, 65 (Suppl. 1), 2015, 1 page.

Morsing M., et al., "Evidence of Two Distinct Functionally Specialized Fibroblast Lineages in Breast Stroma," Breast Cancer Research, vol. 18, 2016, pp. 1-11.

Narayan S., et al., "OCT4 and SOX2 Work as Transcriptional Activators in Reprogramming Human Fibroblasts," Cell Reports, Aug. 15, 2017, 27 pages.

Office Communication issued in Canadian Patent Application No. 3,119,259, dated Feb. 1, 2024, 6 pages.

Official Communication issued in Canadian Patent Application No. 3118760, mailed Dec. 13, 2024, 5 pages.

Oguma Y., et al., "Single-Cell RNA Sequencing Reveals Different Signatures of Mesenchymal Stromal Cell Pluripotent-like and Multipotent Populations," Iscience, Nov. 18, 2022, vol. 25, No. 11, 24 pages.

PCT International Search Report and Written Opinion issued in International Application No. PCT/US2021/026752, dated Aug. 12, 2021, 11 Pages.

PCT International Search Report and Written Opinion issued in International Application No. PCT/US/2022/080206, dated Feb. 21, 2023, 12 pages.

Rana N.K., et al., "CoCI2 Simulated Hypoxia Induce Cell Proliferation and Alter the Expression Pattern of Hypoxia Associated Jenes Involved in Angiogenesis and Apoptosis," Biology Research, vol. 52, No. 1, Article 12, 2019, 13 pages.

Rosochowicz M. A., et al., "Conditioned Medium—Is It an Undervalued Lab Waste with the Potential for Osteoarthritis Management?," Stem Cell Reviews and Reports, 2023, vol. 19, pp. 1185-1213.

Rossi L., et al., "Hematopoietic Stem Cell Characterization and Isolation" Methods in Molecular Biology, 2013, 10 pages.

Sharma K. K., et al., "Neuropathy, Its Profile and Experimental Nerve Injury Neuropathic Pain Models: a Review," Current Pharmaceutical Design, 2023, vol. 29, pp. 3343-3356.

Sheng Z., et al., "Efficacy of Minocycline in Acute Ischemic Stroke: A Systemic Review and Meta-Analysis of Rodent and Clinical Studies," Frontiers in Neurology, 2018, 9(1103), 12 pages.

Shi, P. et al. "Therapeutic Effects of Cell Therapy with Neonatal Human Dermal Fibroblasts and Rabbit Dermal Fibroblasts on Disc Degeneration and Inflammation, " The Spine Journal, vol. 18, 2018, p. 111.

Shinotsuka N., et al., "Fibroblasts: the Neglected Cell Type in Peripheral Sensitisation and Chronic Pain a Review Based on a Systematic Search of the Literature," BMJ Open Science. 2022;6:e100235. DOI: 10.1136/bmjos-2021-100235, 11 pages.

Stappenbeck T.S., et al., "The Role of Stromal Stem Cells in Tissue Regeneration and Wound Repair," Science, Jun. 26, 2009, vol. 324, No. 5935, doi:10.1126/science. 1172687, ISSN 0036-8075, pp. 1666-1669, Retrieved from the Internet: URL: http://dx.doi.org/10.1126/science.1172687.

Sun D, et al., "Basic Fibroblast Growth Factor-enhanced Neurogenesis Contributes to Cognitive Recovery in Rats Following Traumatic Brain Injury," Experimental Neurology, Mar. 1, 2009, vol. 216, No. 1, pp. 56-65.

Sun J., et al., "Intranasal Delivery of Hypoxia-preconditioned Bone Marrow-derived Mesenchymal Stem Cells Enhanced Regenerative Effects After Intracerebral Hemorrhagic Stroke in Mice," Experimental Neurology, Oct. 2015, vol. 272, pp. 78-87.

Sun X., et al., "CXCL12/CXCR4/CXCR7 Chemokine Axis and Cancer Progression," Cancer and Metastasis Reviews, Dec. 2010, vol. 29, No. 04, pp. 709-722.

Tang C, et al., "FGF2 Attenuates Neural Cell Death via Suppressing Autophagy After Rat Mild Traumatic Brain Injury," Stem Cells International, 2017, vol. 2017, Article ID 2923182, 11 pages.

(56) References Cited

OTHER PUBLICATIONS

Tassew N.G., et al., "Exosomes Mediate Mobilization of Autocrine Wnt10b to Promote Axonal Regeneration in the Injured CNS," Cell Reports, 2017, 20(1), pp. 99-111.

Teicher B.A., et al., "CXCL12 (SDF-1)/CXCR4 Pathway in Cancer," Clinical Cancer Research, Molecular Pathways, Jun. 1, 2010, vol. 16, No. 11, pp. 2927-2931.

Thau-Zuchman O, et al., "Combination of Vascular Endothelial and Fibroblast Growth Factor 2 for Induction of Neurogenesis and Angiogenesis After Traumatic Brain Injury," May 2012), Journal of Molecular Neuroscience, vol. 47, No. 1, pp. 166-172.

Uchida H., et al., "Transplantation of Unique Subpopulation of Fibroblasts, Muse Cells, Ameliorates Experimental Stroke Possibly via Robust Neuronal Differentiation", Stem Cells, Sep. 28, 2015, vol. 34, No. 01, pp. 160-173.

Vadala G., et al., "Stem Cells Sources for Intervertebral Disc Regeneration," World Journal of Stem Cells, May 26, 2016, vol. 08, No. 05, pp. 185-201.

Wang K.K., et al., "An Update on Diagnostic and Prognostic Biomarkers from Traumatic Brain Injury," Expert Review of Molecular Diagnostics, 2019, 31 pages.

Wang X., et al., "Hypoxia Precondition Promotes Adipose-Derived Mesenchymal Stem Cells Based Repair of Diabetic Erectile Dysfunction via Augmenting Angiogenesis and Neuroprotection," PLoS One, vol. 10, No. 3, Article e0118951, 2015, 18 pages.

Wang Y., et al., "Roles of Chemokine CXCL12 and its Receptors in Ischemic Stroke," Current Drug Targets, Feb. 2012, vol. 13, No. 02, pp. 166-172.

Wernig M., et al., "Neurons Derived from Reprogrammed Fibroblasts Functionally Integrate into the Fetal Brain and Improve Symptoms of Rats with Parkinson's Disease," Proceedings of the National Academy of Science, Apr. 15, 2008, vol. 105, No. 15, pp. 5856-5867.

Weston N.M., et al., "The Potential of Stem Cells in Treatment of Traumatic Brain Injury," Current Neurology and Neuroscience Reports, Jan. 25, 2018, 17 pages.

Wikipedia, "Muscle," Wikipedia.com, Mar. 30, 2018, 2 pages.

Wong T., et al., "The Role of Fibroblasts in Tissue Engineering and Regeneration," British Journal of Dermatology, Jun. 1, 2007, vol. 156, No. 06, pp. 1149-1155.

Yamashita et al., "Non-Tumorigenic Pluripotent Reparative Muse Cells Provide a New Therapeutic Approach for Neurologic Diseases," Cells, 10:961, 2021, 21 Pages.

Yoder M.C., "Endothelial Stem and Progenitor Cells," (Stem Cells): (2017 Grover Conference Series), Pulmonary Circulation, Nov. 3, 2017, 9 pages.

Zeddou M., et al., "Umbilical Cord Fibroblasts: Could They Be Considered As Mesenchymal Stem Cells?," World J Stem Cells (World Journal of Stem Cells, 2014, vol. 6, No. 3, pp. 367-370.

Zhao B., et al., "Hypoxia drives the transition of human dermal fibroblasts to a myofibroblast- like phenotype via the TGF-b1/Smad3 pathway," International Journal of Molecular Medicine, vol. 39, 2017, pp. 153-159.

* cited by examiner

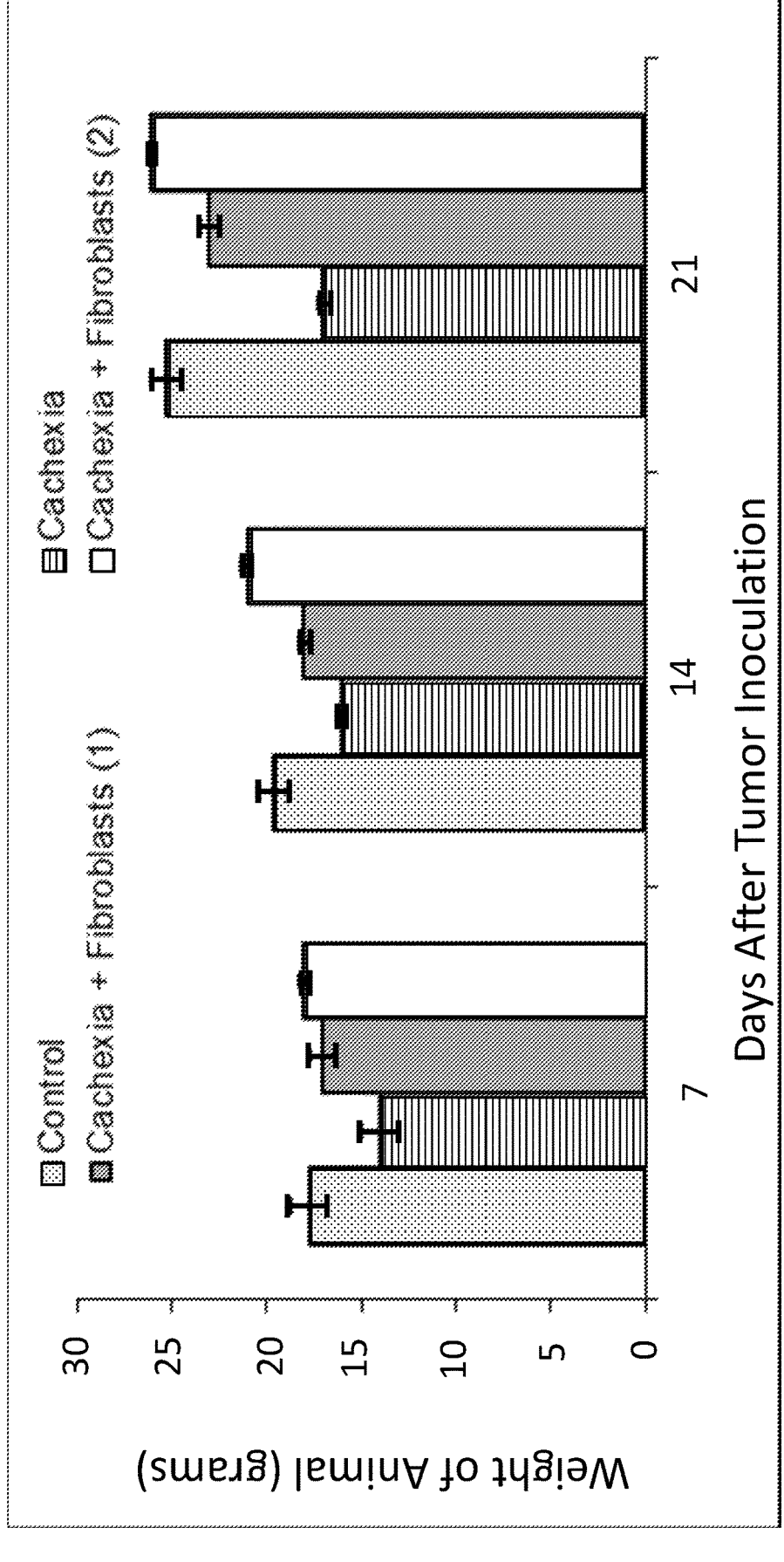

TREATMENT OF CACHEXIA USING FIBROBLAST CELLS AND PRODUCTS THEREOF

This application is a national phase application under 35 U.S.C. § 371 that claims priority to International Application No. PCT/US2019/059678 filed Nov. 4, 2019, which claims priority to U.S. Provisional Patent Application Ser. No. 62/755,542, filed Nov. 4, 2018, both of which areis incorporated by reference herein in theirits entirety.

TECHNICAL FIELD

The present disclosure concerns at least the fields of cell biology, molecular biology, cell therapy, and medicine.

BACKGROUND

Cachexia is a condition associated with muscle wasting particularly presenting in patients with cancer or chronic infections such as HIV, for example. Although studies have shown that inflammatory mediators are causative of cachexia, such as TNF-alpha, interventions to inhibit inflammation have been relatively ineffective in clinical situations. One potential reason for this disparity, is the multifactorial nature of cancer-associated inflammation.

The process of neoplastic transformation is associated with uncontrolled proliferation of cells, which gives rise to necrosis of de novo tissues, resulting in macrophage infiltration, complement activation, and neo-angiogenesis. In situations where this manifestation of neoplasia is occurring at a level where normal physiological processes are disturbed, systemic increases in inflammatory markers are observed, which give rise to exaggerated chronic inflammation that presents systemic consequences to the overall constitution of the patient.

The majority of cancer patients succumb to disease because of muscle wasting, metabolic abnormalities, and multiple organ failure. Although currently available interventions are focused on reducing tumor burden in a cancer patient, there is a need in the art for interventions which reduce pathologies associated with the impact of tumor masses on the general physiology of the patient. The present disclosure provides means for using fibroblasts to restore physiological, immunological and metabolic homeostasis in cancer patients, which allows for the possibility of innate and adaptive host responses to initiate, maintain, and execute activities which result in tumor stabilization and in some cases regression.

BRIEF SUMMARY

Embodiments of the disclosure include methods for ameliorating cachexia, or inflammation related thereto, in an individual, comprising the steps of administering an effective amount of immune-modulating fibroblasts to the individual. The methods may also include culturing a population of fibroblasts under suitable conditions to induce production of immune-modulating activity, thereby producing the immune-modulating fibroblasts. The cachexia, or inflammation related thereto, may be initiated by a chronic inflammatory condition such as one selected from the group consisting of chronic infection, tuberculosis, HIV/AIDS, cancer, coeliac disease, chronic obstructive pulmonary disease, multiple sclerosis, rheumatoid arthritis, congestive heart failure, familial amyloid polyneuropathy, mercury poisoning (acrodynia), Crohn's disease, untreated/severe type 1 diabetes mellitus, anorexia nervosa, hormonal deficiency, and a combination thereof. In some cases, the chronic inflammatory condition is associated with the elevation of one or more detectable markers, such as one or more markers detected in the bloodstream. The individual may be known to have the chronic inflammatory condition or may be suspected of having or at risk for having a chronic inflammatory condition. Examples of detectable markers include those selected from the group consisting of C-reactive protein, Interleukin-1, Interleukin-6, TNF-alpha, and a combination thereof.

In particular embodiments of the disclosure, the fibroblasts utilized in methods are derived from amniotic fluid. Examples of fibroblasts derived from amniotic fluid may be those selected from the species from the group consisting of humans, primates, dogs, cats, goats, elephants, cattle, horses, pigs, mice, rabbits, and a combination thereof. In specific embodiments, the fibroblasts express detectable levels of one or more markers selected from the group consisting of SSEA3, SSEA4, Tra-1-60, Tra-1-81, Tra-2-54, Oct-4, CD13, CD44, CD49b, CD105, aminopeptidase N, and a combination thereof. In specific examples, the fibroblasts do not express detectable levels of SSEA1.

When an individual is provided fibroblasts, they may be administered to the individual affected by cachexia, or inflammation related thereto, by one or more routes selected from the group consisting of epidural, intracerebral, intracerebroventricular, epicutaneous, sublingual, buccal extraamniotic, nasal, intraarterial, intracardiac, intracavernous, intradermal, intralesional, intramuscular, intraocular, intraosseous, intraperitoneal, intrathecal, intrauterine, intravaginal, intravenous, intravesical, intravitreal, subcutaneous, transdermal, perivascular, transmucosal, and a combination thereof.

The present disclosure encompasses the use of fibroblast cells possessing regenerative properties, tissues associated with the cells possessing regenerative properties, and products derived from cells possessing regenerative properties for the treatment of cachexia or inflammation related thereto. In one embodiment, cancer-associated cachexia or HIV-associated cachexia (for example) are treated by administration of cells or tissues possessing regenerative cells that have been modified to allow for administration, while retaining properties associated with cellular regeneration. The administration may be in a manner that in some cases is intravenous, subcutaneous or intramuscular.

In embodiments of the disclosure, there are methods for ameliorating cachexia, or inflammation related thereto, in an individual, comprising the steps of: a. culturing a population of fibroblasts under suitable conditions to induce production of immune-modulating activity, thereby producing immune-modulating fibroblasts; and b. administering an effective amount of said immune-modulating fibroblasts to the individual. In specific embodiments, the cachexia, or inflammation related thereto, is initiated by a chronic inflammatory condition, such as is selected from the group consisting of chronic infection, tuberculosis, HIV/AIDS, cancer, coeliac disease, chronic obstructive pulmonary disease, multiple sclerosis, rheumatoid arthritis, congestive heart failure, familial amyloid polyneuropathy, mercury poisoning (acrodynia), Crohn's disease, untreated/severe type 1 diabetes mellitus, anorexia nervosa, hormonal deficiency, and a combination thereof. In specific embodiments, the chronic inflammatory condition is associated with the elevation of one or more detectable markers, such as detectable markers selected from the group consisting of C-reactive protein, Interleukin-1, Interleukin-6, TNF-alpha, and a combination thereof. In specific embodiments, fibroblasts are derived from amniotic fluid, such as amniotic fluid selected from the species from the group consisting of humans, primates, dogs, cats, goats, elephants, cattle, horses, pigs, mice, rabbits, and a combination thereof. The fibroblasts may express detectable levels of one or more markers selected from the group consisting of SSEA3, SSEA4, Tra-1-60, Tra-1-81, Tra-2-54, Oct-4, CD13, CD44, CD49b, CD105, aminopeptidase N, and a combination thereof. In specific embodiments, the ibroblasts do not express detectable levels of SSEA1.

10. The method of any one of claims 1-10, wherein said fibroblasts are administered to the individual affected by cachexia, or inflammation related thereto, by one or more routes selected from the group consisting of epidural, intracerebral, intracerebroventricular, epicutaneous, sublingual, buccal extra-amniotic, nasal, intraarterial, intracardiac, intracavernous, intradermal, intralesional, intramuscular, intraocular, intraosseous, intraperitoneal, intrathecal, intrauterine, intravaginal, intravenous, intravesical, intravitreal, subcutaneous, transdermal, perivascular, transmucosal, and a combination thereof.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWING

For a more complete understanding of the present disclosure, reference is now made to the following descriptions taken in conjunction with the accompanying drawing.

FIG. 1. Treatment of cachexia using skin foreskin fibroblasts. The weight of particular mice exposed to different conditions was measured. From left to right for each of the groupings of four bars: 1) control mice (Ctrl group) injected subcutaneously with PBS in the right flank of axilla; 2) cachectic mice (CA group) injected subcutaneously with $1 \times 10^6$ LLC cells in the right flank of axilla; 3) cachectic mice treated with 100,000 foreskin fibroblasts (Cachexia+Fibroblasts (1)); and 4) 200,000 foreskin fibroblasts (Cachexia+Fibroblasts (2)).

DETAILED DESCRIPTION

I. Definitions

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein embodiments which are disclosed and still obtain a like or similar result without departing from the spirit and scope of the disclosure. The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

"Subject" and "patient" and "individual" refer to either a human or non-human, such as primates, mammals, and vertebrates. In particular embodiments, the subject is a human, dog, cat, horse, cow, and so forth.

"Treating" or treatment of a disease or condition refers to executing a protocol, which may include administering one or more drugs or therapies (including cells) to a patient, in an effort to alleviate at least one sign or symptom of the disease. Desirable effects of treatment include decreasing the rate of disease progression, ameliorating or palliating the disease state, delaying the onset of at least one symptom, and remission or improved prognosis. Alleviation can occur prior to signs or symptoms of the disease or condition appearing, as well as after their appearance, or both. Thus, "treating" or "treatment" may include "preventing" or "prevention" of disease or undesirable condition. In addition, "treating" or "treatment" does not require complete alleviation of one or more signs or symptoms, does not require a cure, and specifically includes protocols that have only a marginal effect on the patient.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

Cachexia refers to the unintended loss of weight associated with cancer, infectious disease and other catabolic states that cannot be reversed with nutritional support. Cachexia frequently accompanies the terminal course in patients suffering from various chronic diseases such as end-stage chronic heart failure, advanced cancer, chronic kidney disease, chronic obstructive pulmonary disease (COPD), HIV, and rheumatoid arthritis, for example. Aside from excessive weight loss, additional symptoms include anorexia, malabsorption, nausea, asthenia, neuroendocrine changes, immune system function impairment, and disruption of energy metabolism. Several methods for treating cachexia have been suggested, however, the focus has been on developing therapies directed at the underlying illness. To date, no direct treatment for cachexia is available.

Recently, there has been some level of success in better understanding the multifactorial nature of cachexia, particularly with the role of inflammatory mediators in the initiation and perpetuation of this condition. Much of this knowledge stems from earlier studies implicating bacterial lipopolysaccharides (LPS), or endotoxins, in the pathophysiological manifestations of bacterial infection, sepsis and critical illness. Recently, it was observed that cytokines derived from the macrophage/monocyte lineage can mimic the effects of many endotoxins and are central mediators responsible for the clinical phenotype of cachexia.

The present disclosure pertains to the use of fibroblasts as a means of reducing cachexia in an individual in need of therapy. More particularly, the disclosure pertains to the use of fibroblasts in reducing cachexia or inflammation-associated cachexia. More particularly, the disclosure provides means of augmenting activity of certain cells to prevent or treat cachexia in a patient in need of therapy. The treated individual may be an aging patient, the individual may be a cancer patient, the individual may be a patient infected with viral or other infections and/or the individual may be a patient with a medical disorder or disease having cachexia as a symptom. The individual may be of any age, gender, or race.

In particular embodiments, the disclosure provides for administration of regenerative cells, in one embodiment, fibroblasts, for the inhibition of cachexia or reduction in severity of at least one symptom of cachexia and/or delay in onset of cachexia. In specific embodiments, upon administration of an effective amount of fibroblasts to an individual, the fibroblasts are capable of suppressing tumor-derived molecules capable of inducing muscle atrophy and immune inhibition.

Embodiments of the disclosure include methods for ameliorating cachexia, or inflammation related thereto, in an individual, comprising the steps of optionally culturing a population of fibroblasts under suitable conditions to induce production of immune-modulating activity, thereby producing immune-modulating fibroblasts; and administering an effective amount of immune-modulating fibroblasts to the individual.

In particular embodiments, there are methods of increasing the weight of an individual that has cachexia, or preventing weight loss of an individual at risk for cachexia, comprising the step of providing to the individual an effective amount of fibroblasts, including immune-modulating fibroblasts. In specific embodiments, the fibroblasts express detectable levels of one or more markers selected from the group consisting of SSEA3, SSEA4, Tra-1-60, Tra-1-81, Tra-2-54, Oct-4, CD13, CD44, CD49b, CD105, aminopeptidase N, and a combination thereof.

The disclosure encompasses fibroblasts of any kind, for example, foreskin-derived fibroblasts, that are capable of secreting factors that inhibit inflammation, and thereby suppress the ability of the host body to induce muscle wasting. The cells may be immortal in culture, maintain euploidy for >1 year in culture, share one or more markers with human embryonic stem cells, and/or may be capable of differentiating into all three germ layers of the developing embryo: Endoderm, Mesoderm and Ectoderm.

In one embodiment, fibroblasts are derived from amniotic fluid, wherein the cells are extracted from the amnion harvested during the second trimester of human pregnancies. It is known that amniotic fluid comprises multiple morphologically-distinguishable cell types, and the majority of the cells are prone to senescence and are lost from cultures. In one embodiment, fibronectin-coated plates and culture conditions described in U.S. Pat. No. 7,569,385 (incorporated by reference herein in its entirety) are used to grow cells from amniotic fluid harvests from normal 16-18 week pregnancies. The cells of the disclosure may be of fetal origin, and have a normal diploid karyotype. Growth of the amniotic fluid-derived fibroblasts as described in the disclosure for use in neurological ischemic conditions results in cells that are multipotent, as several main cell types have been derived from them. As used herein, the term "multipotent" refers to the ability of amniotic fluid regenerative cells to differentiate into several main cell types. The amniotic fluid derived fibroblasts may also be propagated under specific conditions to become "pluripotent." The term "pluripotent stem cells" describes stem cells that are capable of differentiating into any type of body cell, when cultured under conditions that give rise to the particular cell type. The amniotic fluid regenerative cells may be isolated from humans. However, the amniotic fluid regenerative cells may be isolated in a similar manner from other species. Examples of species that may be used to derive the amniotic fluid regenerative cells include but are not limited to mammals, humans, primates, dogs, cats, goats, elephants, endangered species, cattle, horses, pigs, mice, rabbits, and the like.

An amniotic fluid-derived fibroblast cell can be recognized by their specific cell surface proteins or by the presence of specific cellular proteins, in at least specific cases. Typically, specific cell types have specific cell surface proteins. These surface proteins can be used as "markers" to determine or confirm specific cell types. Typically, these surface markers can be visualized using antibody-based technology or other detection methods. Surface markers of the isolated amniotic fluid-derived fibroblasts cells extracted from independently-harvested amniotic fluid samples were tested for a range of cell surface and other markers, using monoclonal antibodies and FACS analysis. These cells can be characterized by the following cell surface markers: SSEA3, SSEA4, Tra-1-60, Tra-1-81, Tra-2-54, or a combination thereof. The fibroblast cells can be distinguished from mesenchymal cells in that the mesenchymal cells do not express the cell surface marker SSEA1. Additionally, fibroblasts may express the stem cell transcription factor, Oct-4. The fibroblast cells can be recognized by the presence of at least one, or at least two, or at least three, or at least four, or at least five, or at least six, or all of the following cellular markers, in some cases: SSEA3, SSEA4, Tra-1-60, Tra-1-81, Tra-2-54 and/or Oct-4, in specific embodiments.

In certain embodiments, fibroblasts of the disclosure in culture express very little or no SSEA-1 marker. In addition to the embryo stem cell markers SSEA3, SSEA4, Tra1-60, Tra1-81, Tra2-54, and Oct-4, the amniotic fluid-derived fibroblasts also expressed high levels of the cell surface antigens that are normally found on human mesenchymal stem cells, but not normally on human embryo stem cells (M F Pittinger et al., Science 284:143-147, 1999; S Gronthos et al., J. Cell Physiol. 189:54-63, 2001). This set of markers includes CD13 (99.6%) aminopeptidase N, CD44 (99.7%) hyaluronic acid-binding receptor, CD49b (99.8%) collagen/laminin-binding integrin alpha2, and CD105 (97%) endoglin. Presence of both the embryonic stem cell markers and the hMSC markers on the fibroblast cell cultures indicates that amniotic fluid-derived fibroblast cells, grown and propagated as described here, represent a novel class of human stem cells.

In some embodiments of the disclosure, at least about 90%, 91%, 92%, 93%, 94%, 95%, 96%, 97%, 98%, 99%, or 100% of fibroblast cells in a culture express CD13. In some embodiments, at least about 90%, 91%, 92%, 93%, 94%, 95%, 96%, 97%, 98%, 99%, or 100% of the cells in the culture express CD44. In some embodiments of the disclosure, a range from at least about 90%, 91%, 92%, 93%, 94%, 95%, 96%, 97%, 98%, 99%, or 100% of the cells in the culture express CD49b. In certain embodiments of the disclosure, at least about 90%, 91%, 92%, 93%, 94%, 95%, 96%, 97%, 98%, 99%, or 100% of the cells in the culture express CD105. In certain embodiments of the disclosure, at least about 90%, 91%, 92%, 93%, 94%, 95%, 96%, 97%, 98%, 99%, or 100% of the cells in the culture express SSEA3. In certain embodiments of the disclosure, at least about 90%, 91%, 92%, 93%, 94%, 95%, 96%, 97%, 98%, 99%, or 100% of the cells in the culture express SSEA4. In some embodiments of the disclosure, at least about 90%, 91%, 92%, 93%, 94%, 95%, 96%, 97%, 98%, 99%, or 100% of the cells in the culture express Tra-1-60. In particular embodiments of the disclosure, at least about 90%, 91%, 92%, 93%, 94%, 95%, 96%, 97%, 98%, 99%, or 100% of the cells in the culture express Tra-1-81. In certain embodiments of the disclosure, at least about 90%, 91%, 92%, 93%, 94%, 95%, 96%, 97%, 98%, 99%, or 100% of the cells in the culture express Tra-2-54. In particular embodiments of the disclosure, at least about 90%, 91%, 92%, 93%, 94%, 95%, 96%, 97%, 98%, 99%, or 100% of the cells in the culture express Oct-4. In certain embodiments of the disclosure, at least about 90%, 91%, 92%, 93%, 94%, 95%, 96%, 97%, 98%, 99%, or 100% of the cells in the culture express aminopeptidase N.

A "nutrient medium" is a medium for culturing cells containing nutrients that promote proliferation and may be utilized in embodiments of the disclosure. The nutrient medium may comprise any of the following in an appropriate combination: isotonic saline, buffer, amino acids, antibiotics, serum or serum replacement, and exogenously added factors.

General methods relating to stem cell differentiation techniques that may be useful for differentiating the amniotic fluid regenerative cells into fibroblasts of this disclosure can be found in general texts such as: Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998); and in Stem cell biology (L. M. Reid, Curr. Opinion Cell Biol. 2:121, 1990), each of which is incorporated by reference herein in its entirety.

In one embodiment of the disclosure, fibroblast cells are used to treat cachexia associated with aging. In another embodiment, cachexia-associated factors are used to guide the dose of fibroblasts provided to a patient in which cachexia is aimed to be treated. In another embodiment, fibroblasts used comprise amniotic fluid-derived fibroblast cells, and in some cases the fibroblast cells are administered intravenously. In another embodiment, amniotic membrane-derived fibroblast cells are administered. Amniotic membranes may be used as a source of fibroblast cells by direct administration. In one embodiment fibroblasts are administered a concentration of 10-200 million cells intravenously.

Administration of cachexia-inhibiting cells to a mammalian patient can be by any route, including but not limited to intravenous, intradermal, transdermal, subcutaneous, intramuscular, inhalation (e.g., via an aerosol), buccal (e.g., sub-lingual), topical (i.e., both skin and mucosal surfaces, including airway surfaces), intrathecal, intraarticular, intraplural, intracerebral, intra-arterial, intraperitoneal, oral, intralymphatic, intranasal, rectal or vaginal administration, by perfusion through a regional catheter, or by direct intralesional injection.

In a particular embodiment, the compositions of the disclosure are administered by intravenous push or intravenous infusion given over defined period (e.g., 0.5 to 2 hours). The compositions of the disclosure can be delivered by peristaltic means or in the form of a depot, although a suitable route in any given case will depend, as is well known in the art, on such factors as the species, age, gender and overall condition of the subject, the nature and severity of the condition being treated and/or on the nature of the particular composition (i.e., dosage, formulation) that is being administered. In particular embodiments, the route of administration is via bolus or continuous infusion over a period of time, once or twice a week.

In particular embodiments, the route of administration is by subcutaneous injection given in one or more sites (e.g., thigh, waist, buttocks, arm), optionally once or twice weekly. In one embodiment, the compositions, and/or methods of the disclosure are administered on an outpatient basis. Those skilled in the art will appreciate that dosages can be selected based on a number of factors including the age, sex, species and condition of the subject (e.g., activity of cachexia or inflammation related thereto), the desired degree of cachexia or inflammation related thereto to be treated can be determined by one of skill in the art. For example, effective amounts of the compositions of the disclosure may be extrapolated from dose-response curves derived from in vitro test systems or from animal model (e.g. the cotton rat or monkey) test systems.

Examples of dosing regimens that can be used in the methods of the disclosure include, but are not limited to, daily, three times weekly (intermittent), weekly, or every 14 days. In certain embodiments, dosing regimens include, but are not limited to, monthly dosing or dosing every 6-8 weeks. Those skilled in the art will appreciate that dosages are generally higher and/or frequency of administration greater for initial treatment as compared with maintenance regimens.

In some embodiments, an individual at the onset of a medical condition that is associated with cachexia begins being subjected to methods of the disclosure. The methods of the disclosure may or may not be provided to the individual at substantially the same time as one or more treatments for the medical condition. In some cases, the individual is subjected to methods of the disclosure when a symptom of cachexia becomes detectable. The fibroblasts of the disclosure may be provided to the individual before, during, and/or after any treatment for the medical condition.

Embodiments of the disclosure include methods of treating cachexia or inflammation related thereto, comprising the steps of optionally identifying an individual suffering from weight loss or cachexia; and administering to the individual an effective amount of (1) a fibroblast cell population; (2) a tissue comprising a fibroblast cell population, and/or (3) products produced by a fibroblast cell population and/or a tissue comprising a fibroblast cell population. The cachexia may or may not be associated with muscle wasting. The cachexia may or may not be associated with a neoplasia; an inflammatory condition; a chronic infection; tuberculosis; or HIV, for example. In at least some cases, an individual exhibits an elevation of one or more markers associated with chronic inflammation. An example of a marker associated with chronic inflammation includes an elevation of C-reactive Protein, interleukin-1, interleukin-6, and/or TNF-alpha, for example in peripheral blood as compared to age-matched controls. The fibroblasts may be derived from any source, but in specific embodiments they are derived from foreskin. In at least some cases, the fibroblasts are capable of adhering to plastic. The fibroblasts may be administered to the individual in the form of a morselized amniotic membrane tissue that may or may not be treated in a manner to stimulate upregulation of growth factor production, said growth factors stimulatory of anti-cachectic activities. In specific cases, such treatment comprises exposure to hypoxic conditions, acidic conditions, hypotonic conditions, or a combination thereof). The fibroblasts may or may not be administered in the form of a single cell suspension.

In particular methods of the disclosure, fibroblasts are utilized in an individual in need thereof to prevent, delay the onset of, or reduce the severity of muscle wasting (with or without accompanying cachexia), metabolic abnormalities, and multiple organ failure. When there is a delay in the onset of muscle wasting, cachexia, metabolic abnormalities, and/ or multiple organ failure, the delay may be in the order of weeks, years, or months, for example.

The amount of any types of cells for administration to an individual may depend on the severity of the cachexia to be treated and/or of the type of cells to be injected for the treatment. The cells may be prepared for administration in a pharmaceutically acceptable carrier, for example a sterile saline isotonic solution. In some embodiments, the pharmaceutically acceptable carrier may comprise one or more additional agents, such as FAS ligand, IL-2R, IL-1 Ra, IL-2, IL-4, IL-8, IL-10, IL-20, IL-35, HLA-G, PD-L1, I-309, IDO, iNOS, CD200, Galectin 3, sCR1, arginase, PGE-2, aspirin, atorvastatin, fluvastatin, lovastatin, pravastatin, rosuvastatin, simvastatin, pitavastatin, n-acetylcysteine, rapamycin, IVIG, naltrexone, TGF-beta, VEGF, PDGF, CTLA-4, anti-CD45RB antibody, hydroxychloroquine, leflunomide, auranofin, dicyanogold, sulfasalazine, methotrexate, glucocorticoids, etanercept, adalimumab, abatacept, anakinra, certolizumab, Etanercept-szzs, golimumab, infliximab, rituximab, tocilizumab, cyclosporine, IFN-gamma, everolimus, rapamycin, VEGF, FGF-1, FGF-2, angiopoietin, HIF-1-alpha, or a combination thereof.

In one embodiment of the disclosure, fibroblasts are administered to a subject by any suitable route, including by injection (such as intramuscular injection), including in hypoxic areas. Suitable routes include intravenous, subcutaneous, intrathecal, oral, intrarectal, intrathecal, intraomentral, intraventricular, intrahepatic, and intrarenal.

In certain embodiments, fibroblasts may be derived from tissues comprising skin, heart, blood vessels, bone marrow, skeletal muscle, liver, pancreas, brain, adipose tissue, foreskin, placental, and/or umbilical cord. In specific embodiments, the fibroblasts are placental, fetal, neonatal or adult or mixtures thereof.

The number of administrations of cells to an individual will depend upon the factors described herein at least in part and may be optimized using routine methods in the art. In specific embodiments, a single administration is required. In other embodiments, a plurality of administration of cells is required. It should be appreciated that the system is subject to variables, such as the particular need of the individual, which may vary with time and circumstances, the rate of loss of the cellular activity as a result of loss of cells or activity of individual cells, and the like. Therefore, it is expected that each individual could be monitored for the proper dosage, and such practices of monitoring an individual are routine in the art.

In one embodiment of the disclosure, cells (such as fibroblasts) are cultured ex vivo using means known in the art for preserving viability and proliferative ability of the cells. In specific embodiments for fibroblasts, there may be modification of known culture techniques to achieve one or more desired effects for the cells, such as to decrease visibility of fibroblasts to a recipient immune system. In one embodiment, cells (for example, fibroblasts) are cultured in conditions that lack one or more xenogeneic components, such as fetal calf serum. In specific embodiments, the disclosure encompasses the substitution of fetal calf serum with human platelet rich plasma, platelet lysate, umbilical cord blood serum, autologous serum, and/or defined cytokine mixes as an additional feature, for example to reduce the immunogenicity of the cells (such as fibroblasts).

EXAMPLE

The following example is included to demonstrate certain non-limiting aspects of the disclosure. It should be appreciated by those of skill in the art that the techniques disclosed in the examples that follow represent techniques discovered by the inventors to function well in the practice of the disclosed subject matter. However, those of skill in the art should, in light of the present disclosure, appreciate that many changes can be made in the specific embodiments that are disclosed and still obtain a like or similar result without departing from the spirit and scope of the disclosed subject matter.

Example 1

Treatment of Cachexia Using Skin Foreskin Fibroblasts

Lewis lung carcinoma (LLC) cells were obtained from American Type Culture Collection (ATCC) and were cultured at 37° C. with 5% $CO_2$ using Dulbecco's modified Eagle's medium containing 10% fetal bovine serum (Gibco; Thermo Fisher Scientific, Waltham, Ma., USA) and 1% penicillin/streptomycin (Boster Biological Technology, Wuhan, China). Before tumor inoculation, LLC cells were centrifuged at 1000 rpm at 4° C. for 5 min and resuspended in phosphate buffer saline (PBS).

Specific pathogen-free C57BL/6 mice aged 5-6 weeks were housed free for chow and water in the condition of stable temperature and humidity with a regular 12-h light-dark cycle under the specific pathogen-free environment. C57BL/6 mice were randomly assigned into three groups (7 mice per group): 1) control mice (Ctrl group) injected subcutaneously with PBS in the right flank of axilla; 2) cachectic mice (CA group) injected subcutaneously with $1\times10^6$ LLC cells in the right flank of axilla; 3) cachectic mice treated with 100,000 foreskin fibroblasts (ATCC) (Cachexia+Fibroblasts (1)); and 4) 200,000 foreskin fibroblasts (Cachexia+Fibroblasts (2)). The body weight of each mouse and cumulative food intake (combined of all seven mice in each group) were monitored every 3 days following tumor implantation.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for ameliorating cachexia, or inflammation related thereto, in an individual, comprising administering an effective amount of immune-modulating fibroblasts to the individual; wherein the fibroblasts express detectable levels of one or more markers selected from the group consisting of SSEA3, SSEA4, Tra-1-60, Tra-1-81, Tra-2-54, Oct-4, CD13, CD44, CD49b, CD105, aminopeptidase N, and a combination thereof; and administered in the form of a single cell suspension.

2. The method of claim 1, wherein said cachexia, or inflammation related thereto, is initiated by a chronic inflammatory condition.

3. The method of claim 1, wherein said cachexia, or inflammation related thereto, is initiated by a condition selected from the group consisting of chronic infection, tuberculosis, human immunodeficiency virus/acquired immunodeficiency syndrome (HIV/AIDS), cancer, coeliac disease, chronic obstructive pulmonary disease, multiple sclerosis, rheumatoid arthritis, congestive heart failure, familial amyloid polyneuropathy, mercury poisoning (acrodynia), Crohn's disease, untreated/severe type 1 diabetes mellitus, anorexia nervosa, hormonal deficiency, and a combination thereof.

4. The method of claim 2, wherein said chronic inflammatory condition is associated with the elevation of one or more detectable markers.

5. The method of claim 4, wherein said detectable markers are selected from the group consisting of C-reactive protein, Interleukin-1, Interleukin-6, TNF-alpha, and a combination thereof.

6. The method of claim 1, wherein said fibroblasts are derived from cells isolated from amniotic fluid.

7. The method of claim 6, wherein said amniotic fluid is selected from the species from the group consisting of humans, primates, dogs, cats, goats, elephants, cattle, horses, pigs, mice, rabbits, and a combination thereof.

8. The method of claim 1, wherein said fibroblasts do not express detectable levels of SSEA1.

9. The method of claim 1, wherein said fibroblasts are administered to the individual affected by cachexia, or inflammation related thereto, by one or more routes selected from the group consisting of epidural, intracerebral, intracerebroventricular, epicutaneous, sublingual, buccal extra-amniotic, nasal, intraarterial, intracardiac, intracavernous, intradermal, intralesional, intramuscular, intraocular, intraosseous, intraperitoneal, intrathecal, intrauterine, intravaginal, intravenous, intravesical, intravitreal, subcutaneous, transdermal, perivascular, transmucosal, and a combination thereof.

10. A method of increasing the weight of an individual with cachexia or at risk of having cachexia, comprising the step of administering an effective amount of fibroblasts to the individual; wherein the fibroblasts express detectable levels of one or more markers selected from the group consisting of SSEA3, SSEA4, Tra-1-60, Tra-1-81, Tra-2-54, Oct-4, CD13, CD44, CD49b, CD105, aminopeptidase N, and a combination thereof;, and administered in the form of a single cell suspension.

11. The method of claim 10, wherein the individual is at risk for having cachexia has one or more conditions selected from the group consisting of tuberculosis, HIV/AIDS, cancer, coeliac disease, chronic obstructive pulmonary disease, multiple sclerosis, rheumatoid arthritis, congestive heart failure, familial amyloid polyneuropathy, mercury poisoning (acrodynia), Crohn's disease, untreated/severe type 1 diabetes mellitus, anorexia nervosa, and hormonal deficiency, or a combination thereof.

12. The method of claim 10, wherein the individual at risk for having cachexia has chronic infection.

* * * * *